(12) United States Patent
Wakita

(10) Patent No.: US 7,183,427 B2
(45) Date of Patent: Feb. 27, 2007

(54) PROCESS FOR THE PRODUCTION OF METAL SALTS OF RADICAL-POLYMERIZABLE COMPOUNDS

(75) Inventor: Keiji Wakita, Chiba Prefecture (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 423 days.

(21) Appl. No.: 10/501,118

(22) PCT Filed: Feb. 19, 2003

(86) PCT No.: PCT/JP03/01820

§ 371 (c)(1), (2), (4) Date: Jul. 12, 2004

(87) PCT Pub. No.: WO03/070681

PCT Pub. Date: Aug. 28, 2003

(65) Prior Publication Data

US 2005/0119498 A1  Jun. 2, 2005

(30) Foreign Application Priority Data

Feb. 19, 2002 (JP) .................. 2002-040904

(51) Int. Cl.
C07C 309/00 (2006.01)
C07C 57/02 (2006.01)

(52) U.S. Cl. ........................................ 562/115; 562/598

(58) Field of Classification Search .................... None
See application file for complete search history.

(56) References Cited

FOREIGN PATENT DOCUMENTS

| JP | 47-031924 | * 11/1972 |
| JP | 49-011820 | 2/1974 |
| JP | 3-209388 | 9/1991 |

* cited by examiner

Primary Examiner—Paul A. Zucker
(74) Attorney, Agent, or Firm—Howard & Howard Attorneys, P.C.

(57) ABSTRACT

A method for manufacturing metal salts of radical-polymerizable compounds with reduced amount of water in the below-mentioned component (A) by subjecting an aqueous solution of an alkali-metal salt, alkali earth-metal salt, or a zinc salt of the radical-polymerizable compound (A) to heating under a reduced pressure in the presence of an aqueous polymerization inhibitor for removal of aqueous components by distillation from aforementioned compounds (A).

7 Claims, No Drawings

PROCESS FOR THE PRODUCTION OF METAL SALTS OF RADICAL-POLYMERIZABLE COMPOUNDS

The present invention relates to a novel method for manufacturing metal salts of radical-polymerizable compounds with low content of moisture.

BACKGROUND

Normally, sodium methacrylate, potassium methacrylate, sodium acrylate, potassium acrylate, or similar metal salts of radical-polymerizable compounds, are obtained by neutralizing aqueous solutions of alkali-metal compounds. However, the problem associated with the aforementioned process consists in that it is extremely difficult to produce metal salts of the radical-polymerizable compounds with low moisture content when they are obtained from aqueous compounds. Many suggestions have been made heretofore to overcome this problem of the prior-art. For example, there were attempts to remove water by subjecting water solutions of radical-polymerizable compounds to azeotropic dehydration in the presence of an organic solvent such as toluene. This method, however, cannot produce metal salts of radical-polymerizable compounds of high purity because the process is accompanied by a polymerization reaction that occurs during azeotropic dehydration. Attempts have been made to suppress this polymerization reaction by adding conventional polymerization inhibitors normally used in conjunction with radical-polymerizable compounds, such as hydroquinone, methoxyhydroquinone, phenothiazine, hindered phenol, or the like. However, since all these compounds are oil-soluble, their solubility in water is low, they cannot completely stop polymerization of radical-polymerizable compounds, and, therefore, are unsuitable for obtaining metal salts of radical-polymerizable compounds of high purity.

On the other hand, known in the art is a method for obtaining moisture-free metal salts of a methacrylic acid, wherein an aqueous component is removed by pulverizing an aqueous solution of a methacrylic-acid metal salt in a hot-air circulation drier (see Japanese Laid-Open Patent Application Publication (hereinafter referred to as Kokai") 47-031924 and Kokai 49-011820). However, this method is expensive as it requires the use of specific equipment.

Furthermore, a method is know for manufacturing a water-free potassium methacrylate obtained by neutralizing a methacrylic acid in a methanol solution of a potassium methylate (see Kokai 3-209388). However, the potassium methylate used in this process is an expensive reagent, which is not suitable for realization of low-cost production plans.

THE INVENTION

Based on the study aimed at a solution of the problems of the prior art, the authors arrived at the present invention. It is an object of the present invention to provide a method for high-yield production of high-purity metal salts of radical-polymerizable compounds having a reduced content of aqueous components.

More specifically, the present invention relates to a method for manufacturing metal salts of radical-polymerizable compounds with reduced amount of aqueous components by subjecting an aqueous solution of an alkali-metal salt, alkali earth-metal salt, or a zinc salt of a radical-polymerizable compound (A) selected from the group consisting of a compound represented by the following general formula (1): $R^1$—CH=$CR^2$—COOH (where $R^1$ designates a hydrogen atom, an alkyl group or a phenyl group, and $R^2$ designates a methyl group or a hydrogen atom), a compound represented by the following general formula (2): $R^1$—CH=$CR^2$—$R^3$—COOH (where $R^1$ and $R^2$ are the same as defined above, and $R^3$ designates a phenylene group), a compound represented by the following general formula(3): $R^1$—CH=$CR^2$—$SO_3H$(where $R^1$ and $R^2$ are the same as defined above), and a compound of the following general formula(4): $R^1$—CH=$CR^2$—$R^3$—$SO_3H$ (where $R^1$, $R^2$, and $R^3$ are the same as defined above)to heating under a reduced pressure in the presence of (B) an aqueous polymerization inhibitor selected from L-ascorbic acid, sodium L-ascorbate; erythorbic acid sodium erythorbate; N-phenyl hydroxylamine, aqueous salts of N-phenyl hydroxylamine; 3,5-di-t-butyl-4-hydroxyaniline, aqueous salts of 3,5-di-t-butyl-4-hydroxyaniline; 3,5-di-t-butyl-4-hydroxybenzoic acid, and aqueous salts of 3,5-di-t-butyl-4-hydroxybenzoic acid.

The invention also relates to a method for manufacturing metal salts of radical-polymerizable compounds with reduced amount of aqueous components by subjecting an aqueous solution of an alkali-metal salt, alkali earth-metal salt, or a zinc salt of a radical-polymerizable compound (A) selected from the group consisting of a compound represented by the following general formula) 1): $R^1$—CH=$CR^2$—COOH (where $R^1$ designates a hydrogen atom, an alkyl group, or a phenyl group, and $R^2$ designates a methyl group or a hydrogen atom), a compound represented by the following general formula (2): $R^1$—CH=$CR^2$—$R^3$—COOH (where $R^1$ and $R^2$ are the same as defined above, and $R^3$ designates a phenylene group), a compound represented by the following general formula (3): $R^1$—CH=$CR^2$—$SO_3H$ (where $R^1$ and $R^2$ are the same as defined above), and a compound of the following general formula (4): $R^1$—CH=$CR^2$—$R^3$—$SO_3H$ (where $R^1$, $R^2$, and $R^3$ are the same as defined above) to heating under a reduced pressure in the presence of (B) an aqueous polymerization inhibitor selected from L-ascorbic acid, sodium L-ascorbate; erythorbic acid sodium erythorbate; N-phenyl hydroxylamine, aqueous salts of N-phenyl hydroxylamine; 3,5-di-t-butyl-4-hydroxyaniline, aqueous salts of 3,5-di-t-butyl-4-hydroxyaniline; 3,5-di-t-butyl-4-hydroxybenzoic acid, and aqueous salts of 3,5-di-t-butyl-4-hydroxybenzoic acid.

Thus, the method of the present invention makes it possible to reduce the content of aqueous components and to increase the production yield of high-purity salts, such as alkali-metal salts, alkali-earth salts, or zinc salts of radical-polymerizable compounds. Furthermore, the method prevents occurrence of radical polymerization during the manufacturing process.

BEST MODE FOR CARRYING OUT THE INVENTION

A radical-polymerizable compound that constitutes aforementioned component (A) is selected from the group consisting of a compound represented by the following general formula(1): $R^1$—CH=$CR^2$—COOH (where $R^1$ designates a hydrogen atom, an alkyl group, or a phenyl group, and $R^2$ designates a methyl group or a hydrogen atom), a compound represented by the following general formula (2):$R^1$—CH=$CR^2$—$R^3$—COOH (where $R^1$ and $R^2$ are the same as defined above, and $R^3$ designates a phenylene group), a compound represented by the following general formula(3):

$R^1$—CH=$CR^2$—$SO_3H$ (where $R^1$ and $R^2$ are the same as defined above), and a compound of the following general formula(4): $R^1$—CH=$CR^2$—$R^3$—$SO_3H$ (where $R^1$, $R^2$, and $R^3$ are the same as defined above). In the above formulae, $R^1$ may designate a hydrogen atom, methyl group, ethyl group, propyl group, or a similar alkyl group, of which the hydrogen atom or phenyl group, and in particular hydrogen atom, is most preferable. $R^2$ may designate a methyl group or a hydrogen atom, and $R^3$ may designate a phenylene group.

The aforementioned compounds can be exemplified by a methacrylic acid, acrylic acid, cinnamic acid, o-vinylbenzene-sulfonic acid, p-vinylbenzene-sulfonic acid, p-vinylbenzoic acid, or their derivatives.

Component (A) may also comprise an aqueous solution of an alkali metal salt, alkali-earth metal salt, or a zinc salt of the aforementioned radical-polymerizable compounds. The alkali metal of such salt may comprise lithium, sodium, potassium, or rubidium. Of these, the most preferable are sodium and potassium. Alkali-earth metals can be represented by magnesium, calcium, strontium, and barium. Of these, most preferable are magnesium and calcium. The following are examples of metal salts of the aforementioned radical-polymerizable compounds: sodium methacrylate, potassium methacrylate, calcium methacrylate, magnesium methacrylate, zinc methacrylate, sodium acrylate, potassium acrylate, magnesium acrylate, calcium acrylate, magnesium acrylate, zinc acrylate, sodium cinnamate, calcium cinnamate, sodium p-vinyl benzoate, potassium p-vinyl benzoate, sodium o-vinylbenzene sulfonate, potassium o-vinylbenzene sulfonate, sodium p-vinylbenzene sulfonate, and potassium p-vinylbenzene sulfonate.

Aqueous solutions of metal salts of the aforementioned radical-polymerizable compounds can be easily prepared by conventional methods, e.g., by mixing the radical-polymerizable compounds with aqueous solutions of alkali-metal salts, alkali-earth metal salts, or zinc salts and thus neutralizing the compounds, or by saponifying esters of the aforementioned radical-polymerizable compounds with aqueous solutions of the alkali-metal salts, alkali-earth metal salts, or zinc salts.

An aqueous polymerization inhibitor that constitutes component (B) is a specific component of the present invention. This component can be represented by L-ascorbic acid, sodium L-ascorbate, erythorbic acid, sodium erythorbate, or derivatives of the above compounds; N-phenylhydroxylamine, aqueous salts of N-phenyl hydroxylamine; 3,5-di-t-butyl-4-hydroxyaniline, aqueous salts of 3,5-di-t-butyl-4-hydroxyaniline; 3,5-di-t-butyl-4-hydroxybenzoic acid; aqueous salts of 3,5-di-t-butyl-4-hydroxybenzoic acid. The most preferable among the above are L-ascorbic acid (vitamin C), N-phenylhydroxylamine, and hydrochloric salts of N-phenylhydroxylamine, in particular L-ascorbic acid (vitamin C). These compounds are almost completely non-toxic and at the same time are extremely efficient inhibitors of polymerization for radical-polymerizable compounds.

Component (B) should be used in an amount sufficient for inhibiting polymerization of alkali-metal salts, alkali-earth metal salts, or zinc salts of the radical-polymerizable compounds of component (A), but, in general, it is recommended to use them in an amount of 0.001~0.1 parts by weight for each 100 parts by weight of the alkali-metal salts, alkali-earth metal salts, or zinc salts of the radical-polymerizable compounds of component (A). Component (B) can be added at the stage of synthesis of component (A) or after the synthesis of component (A). Addition in the synthesis stage is preferable for the reason of simplicity of the operation.

In accordance with the present invention, aqueous components are removed when component (A) is heated under a reduced pressure in the presence of aforementioned component (B). The use of conventional reaction equipment for this purpose may cause some problems because removal of water from component (A) increases the content of solids and thus hinders stirring. Therefore, components (A) and (B) are first combined with an organic solvent, such as toluene, xylene, heptane, octane, or the like, and then heated for removal of water from component (A) by distillation. Alternatively, components (A) and (B) are heated under a reduced pressure, and, after a major portion of water is removed from component (A), the product is subjected to azeotropic dehydration. The process can be conducted in a mixer-drier suitable for stirring powdered materials, especially for dehydration without addition of organic solvents.

The method of the present invention makes it possible to obtain high-purity salts, such as alkali-metal salts, alkali-earth metal salts, and zinc salts of radical-polymerizable compounds, with high yield and essentially without aqueous components, the content of which does not exceed 5 wt. %, preferably does not exceed 0.5 wt. %, and even more preferably does not exceed 0.2 wt. %.

Thus, as has been mentioned above, the alkali-metal salts, alkali-earth metal salts, and zinc salts of radical-polymerizable compounds produced by the method of the present invention are characterized by high purity and low moisture content. Due to these characteristics, the salts of the present invention are suitable for use as intermediate starting materials in reactions with water-unstable organic compounds. They also can be used as additives to such compounds for improving their physical properties.

EXAMPLES

The invention with be further described in more detail with reference to practical examples.

Example 1

A mixture prepared from 284 g (3.30 moles) of methacrylic acid, 280 g of water, and 500 mg of L-ascorbic acid (vitamin C) was combined with a 48 wt. % aqueous solution of potassium hydroxide and the mixture was stirred to produce an aqueous solution of potassium methacrylate. The obtained aqueous solution was loaded into a mixer-drier and was subjected to dehydration by distillation with heating at 60° C. under a reduced pressure of 20 mmHg. Measurement showed that content of water in the obtained potassium methacrylate did not exceed 0.1 wt. %. The content of water in the product was determined by weighing the distilled water. The potassium methacrylate was obtained with a yield of 98%. The above reaction did not produce any products of polymerization that could be caused by the presence of methacrylic acid.

Example 2

A mixture prepared from 284 g (3.30 moles) of methacrylic acid, 280 g of water, and 500 mg of L-ascorbic acid (vitamin C) was combined with a 48 wt. % aqueous solution of potassium hydroxide and the mixture was stirred to produce an aqueous solution of potassium methacrylate. The obtained aqueous solution was subjected to dehydration by distillation with heating under a reduced pressure of 150 mm Hg. The process was continued until the residual content of water reached 280 g. Following this, the pressure in the reaction system was restored to normal, 600 g of toluene were added, and the product was subjected to azeotropic dehydration to remove the residual moisture and obtain a mixture of potassium methacrylate with toluene. The content of water in potassium methacrylate was 0.03 wt. %. The content of water in the product was determined by means of the Karl Fischer method. The potassium methacrylate was obtained with a yield of 99%. The above reaction did not produce any products of polymerization that could be caused by the presence of methacrylic acid.

Example 3

A mixture prepared from 284 g (3.30 moles) of methacrylic acid, 280 g of water, and 3,5-di-t-butyl-4-hydroxyaniline hydrochloride was combined with a 48 wt. % aqueous solution of potassium hydroxide and the mixture was stirred to produce an aqueous solution of potassium methacrylate. The obtained aqueous solution was loaded into a mixer-drier and was subjected to dehydration by distillation with heating at 60° C. under a reduced pressure of 20 mm Hg. Measurement showed that content of water in the obtained potassium methacrylate did not exceed 0.05 wt. %. The content of water in the product was determined by weighing the distilled water. The potassium methacrylate was obtained with a yield of 97%. The above reaction did not produce any products of polymerization that could be caused by the presence of methacrylic acid.

Example 4

A mixture prepared from 859 g of an aqueous solution of sodium vinylsulfonate (the product of Aldrich Co., 25 wt. % aqueous solution, 1.65 moles of sodium vinylsulfonate) and 300 mg of L-ascorbic acid(vitamin C)was loaded into a mixer-drier and was subjected to dehydration by distillation with heating at 50° C. under a reduced pressure of 10 mmHg. Measurement showed that content of water in the obtained sodium vinylsulfonate did not exceed 0.05 wt. %. The content of water in the product was determined by weighing the distilled water. The sodium vinylsulfonate was obtained with a yield of 96%. The above reaction did not produce any products of polymerization that could be caused by the presence of vinylsulfonic acid.

Comparative Example 1

A mixture was prepared from 284 g (3.30 moles)of methacrylic acid, 280 g of water, and 500 mg of methoxyhydroquinone (MEHQ). The mixture was combined with a 48 wt. % aqueous solution of potassium hydroxide and stirred to produce an aqueous solution of potassium methacrylate. The obtained aqueous solution was subjected to dehydration by distillation with heating under a reduced pressure of 150 mm Hg. The process was carried out until the content of water reached 280 g. Following this, the pressure in the reaction system was restored to normal, 600 g of toluene were added, and the product was subjected to azeotropic dehydration to remove the residual moisture and obtain a potassium methacrylate. The potassium methacrylate was obtained with a yield of 83%. The above reaction system produced a viscous product of polymerization that was caused by the presence of methacrylic acid.

Comparative Example 2

The process for obtaining potassium methacrylate was the same method as in Example 2, with the exception that 2,6-di-t-butyl-4-methylphenol (BHT) was used instead of L-ascorbic acid. In the dehydration process, BHT was distilled out together with water, and azeotropic dehydration produced viscous products of polymerization that hindered stirring and did not allow preparation of the target potassium methacrylate.

The invention claimed is:

1. A method for manufacturing metal salts of radical-polymerizable compounds with a reduced amount of aqueous components by subjecting an aqueous solution of a material selected from the group consisting essentially of an alkali-metal salt, alkali earth-metal salt, and a zinc salt of a radical-polymerizable compound (A) selected from the group consisting of a compound represented by the following general formula(1): $R^1$—CH=$CR^2$—COOH (wherein $R^1$ designates a hydrogen atom, an alkyl group or a phenyl group, and $R^2$ designates a methyl group or a hydrogen atom), a compound represented by the following general formula (2):$R^1$—CH=$CR^2$—$R^3$—COOH wherein $R^1$ and $R^2$ are the same as defined above, and $R^3$ designates a phenylene group, a compound represented by the following general formula (3):$R^1$—CH=$CR^2$—$SO_3$H wherein $R^1$ and $R^2$ are the same as defined above, and a compound of the following general formula (4) :$R^1$—CH=$CR^2$—$R^3$—$SO_3$H wherein $R^1$, $R^2$, and $R^3$ are the same as defined above, to heating under a reduced pressure in the presence of (B) an aqueous polymerization inhibitor for removal of aqueous components by distillation from aforementioned compounds (A).

2. A method for manufacturing metal salts of radical-polymerizable compounds with reduced amount of aqueous components by subjecting an aqueous solution of an alkali-metal salt, alkali earth-metal salt, or a zinc salt of a radical-polymerizable compound (A) selected from the group consisting of a compound represented by the following general formula (1): $R^1$—CH=$CR^2$—COOH (wherein $R^1$ designates a hydrogen atom, an alkyl group, or a phenyl group, and $R^2$ designates a methyl group or a hydrogen atom), a compound represented by the following general formula (2): $R^1$—CH=$CR^2$—$R^3$—COOH (wherein $R^1$ and $R^2$ are the same as defined above, and $R^3$ designates a phenylene group), a compound represented by the following general formula(3): $R^1$—CH=$CR^2$—$SO_3$H (wherein $R^1$ and $R^2$ are the same as defined above), and a compound of the following general formula (4): $R^1$—CH=$CR^2$—$R^3$—$SO_3$H (where $R^1$, $R^2$, and $R^3$ are the same as defined above to heating under a reduced pressure in the presence of (B) an aqueous polymerization inhibitor for removal of aqueous components from aforementioned compounds (A) by distillation, and then adding an organic solvent (D) for azeotropic dehydration.

3. The method according to claim 2, wherein said component (D) is an organic solvent selected from the group consisting essentially of toluene, xylene, heptane, and octane.

4. The method according to claim 1, wherein the content of aqueous components in the metal salts of the radical-polymerizable compounds with a reduced amount of aqueous components does not exceed 5 wt. %.

5. The method according to claim 4, wherein the content of aqueous components in the metal salts of the radical-polymerizable compounds with a reduced amount of aqueous components is within the range of 0 to 0.5 wt. %.

6. The method according to claim 2, wherein the content of aqueous components in the metal salts of the radical-polymerizable compounds with a reduced amount of aqueous components does not exceed 5 wt. %.

7. The method according to claim 6, wherein the content of aqueous components in the metal salts of the radical-polymerizable compounds with a reduced amount of aqueous components is within the range of 0 to 0.5 wt. %.

* * * * *